US010170686B2

(12) United States Patent
Kim et al.

(10) Patent No.: US 10,170,686 B2
(45) Date of Patent: Jan. 1, 2019

(54) ELECTRIC ENERGY HARVESTER USING ULTRASONIC WAVE

(71) Applicant: RESEARCH & BUSINESS FOUNDATION SUNGKYUNKWAN UNIVERSITY, Suwon-si (KR)

(72) Inventors: Sang Woo Kim, Yongin-si (KR); Ronan Hinchet, Suwon-si (KR); Seong Su Kim, Seoul (KR); Wan Chul Seung, Yongin-si (KR); Hong Joon Yoon, Goyang-si (KR); Ju-Hyuck Lee, Suwon-si (KR); Usman Khan, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 299 days.

(21) Appl. No.: 15/200,591

(22) Filed: Jul. 1, 2016

(65) Prior Publication Data

US 2017/0005258 A1 Jan. 5, 2017

(30) Foreign Application Priority Data

Jul. 3, 2015 (KR) ........................ 10-2015-0095180

(51) Int. Cl.
| | | |
|---|---|---|
| *H01L 41/113* | (2006.01) | |
| *B06B 1/02* | (2006.01) | |
| *H02N 2/18* | (2006.01) | |
| *A61N 1/378* | (2006.01) | |

(52) U.S. Cl.
CPC .......... *H01L 41/113* (2013.01); *A61N 1/3787* (2013.01); *B06B 1/0207* (2013.01); *H02N 2/18* (2013.01); *B06B 1/02* (2013.01)

(58) Field of Classification Search
CPC .......... H02N 2/18; H01L 41/113; B06B 1/02; B06B 1/0207
See application file for complete search history.

(56) References Cited

U.S. PATENT DOCUMENTS

| | | | | |
|---|---|---|---|---|
| 8,736,146 | B2* | 5/2014 | Fujii ................... | H01L 41/1136 310/339 |
| 2010/0164433 | A1* | 7/2010 | Janefalkar ............... | H02J 7/025 320/115 |
| 2013/0280557 | A1* | 10/2013 | Lee ....................... | H01M 10/46 429/4 |
| 2016/0233828 | A1* | 8/2016 | Hwang ................. | H01L 41/113 |

FOREIGN PATENT DOCUMENTS

| | | |
|---|---|---|
| KR | 10-2013-0119837 A | 11/2012 |
| KR | 10-2013-0020035 A | 2/2013 |
| KR | 10-2014-082628 A | 7/2014 |

OTHER PUBLICATIONS

Korean Office Action dated Dec. 2, 2015 in counterpart Korean Application No. 10-2015-0095190 (6 pages in Korean).

* cited by examiner

*Primary Examiner* — J. San Martin
(74) *Attorney, Agent, or Firm* — NSIP Law

(57) ABSTRACT

There is provided an electric energy generator system comprising: an ultrasonic-wave emission device configured to generate an ultrasonic-wave and emit the ultrasonic-wave; and an electric energy generator device configured to generate an electric energy upon a receipt of the emitted ultrasonic-wave.

20 Claims, 15 Drawing Sheets

ELECTRIC ENERGY HARVESTER USING ULTRASONIC WAVE

CROSS-REFERENCE TO RELATED APPLICATION

This application claims the benefit of Korea Patent Application No. 10-2015-0095180 filed on, Jul. 3, 2015, the entire content of which is incorporated herein by reference for all purposes as if fully set forth herein.

BACKGROUND

Field of the Present Disclosure

The present disclosure relates to an energy generator system, and, more particularly, to an electric energy generator system using an ultrasonic-wave and to an electric energy generator system configured to generate the electric energy using an ultrasonic-wave in a living body.

Discussion of the Related Art

A conventional electric energy generator device may be buried in the living body to allow a permanent electric energy generation in the body using a blood flow energy, a heart-beat energy, a movement of breast diaphragms, etc.

However, the blood flow energy, heart-beat energy, movement of breast diaphragms, etc. may have a fixed frequency and intensity. This may limit the applications of the conventional electric energy generator device in the body. Further, the blood flow energy, heart-beat energy, movement of breast diaphragms, etc. may have low frequencies and thus low mechanical energies. Further, occurrences of the mechanical energies may be limited to specific regions. Thus, the installation position of the conventional electric energy generator device may be limited to specific position in the body. The conventional electric energy generator device may have a low electric energy generation efficiency.

SUMMARY

Thus, the present applicants have developed an electric energy generator system whose an installation position is not limited to specific position in the body and whose electric energy generation efficiency is higher.

In this connection, the present disclosure provides an electric energy generator system configured to generate the electric energy using an ultrasonic-wave in a living body.

In one aspect, there is provided an electric energy generator system comprising: an ultrasonic-wave emission device configured to generate an ultrasonic-wave and emit the ultrasonic-wave; and an electric energy generator device configured to generate an electric energy upon a receipt of the emitted ultrasonic-wave.

In one embodiment, the ultrasonic-wave emission device comprises: an ultrasonic-wave generator configured to generate the ultrasonic-wave; and ultrasonic-wave emitter configured to emit the generated ultrasonic-wave.

In one embodiment, the electric energy generator device has a closed inner space defined therein and the electric energy generator device is insertable into a living body.

In one embodiment, the electric energy generator device comprises: a substrate; an electrode on the substrate; a first friction-charged member on the electrode; a spacer disposed on the substrate so as to surround the electrode and the first friction-charged member; and a second friction-charged member disposed on the spacer to be spaced from the first friction-charged member, wherein the second friction-charged member repeatedly contacts or is separated from the first friction-charged member, wherein a closed inner space is defined between the first friction-charged member and the second friction-charged member and the spacer, wherein when the electric energy generator device receives the emitted ultrasonic-wave, a pressure in the inner space changes, to allow deformation of the second friction-charged member and thus repetitions of the contact and separation between the first and second friction-charged members, to generate a triboelectric energy.

In one embodiment, the system further comprises a load electrically coupled to the electrode.

In one embodiment, the load includes an electric device, an electronic device or a condenser.

In one embodiment, the system further comprises a rectifier diode electrically coupled to and between the electrode and the load.

In one embodiment, the ultrasonic-wave has an intensity smaller than or equal to 1 W/cm$^2$.

In one embodiment, the ultrasonic-wave has a frequency of 20 kHz to 50 kHz.

In one embodiment, the electric energy generator device comprises: a lower substrate; a lower electrode on the lower substrate; a piezoelectric layer on the lower electrode; an upper electrode on the piezoelectric layer; an insulator disposed on the lower substrate so as to surround the lower electrode, the piezoelectric layer and the upper electrode; and an upper substrate disposed on the upper electrode and the insulator, wherein when the electric energy generator device receives the emitted ultrasonic-wave, the electric energy generator device vibrates and thus the piezoelectric layer deforms to generate an electric energy.

In one embodiment, the electric energy generator device comprises: a lower substrate; a lower electrode on the lower substrate; a first electret on the lower electrode; a spacer disposed on the lower substrate so as to surround the lower electrode and the first electret; a second electret disposed on the spacer to be spaced from the first electret, wherein the first and second electrets have opposite polarization directions to each other; an upper electrode on the second electret; an insulator disposed on the spacer so as to surround the second electret and the upper electrode; and an upper substrate disposed on the upper electrode and the insulator, wherein a closed inner space is defined between the first electret and the second electret and the spacer, wherein when the electric energy generator device receives the emitted ultrasonic-wave, a pressure in the inner space changes, to change a spacing between the first electret and the second electret to generate an electric energy.

In one embodiment, the electric energy generator device comprises: a lower substrate; a lower electrode on the lower substrate; an electret on the lower electrode; a spacer disposed on the lower substrate so as to surround the lower electrode and the electret; an upper electrode disposed on the spacer to be spaced from the electret; an insulator disposed on the spacer so as to surround the upper electrode; and an upper substrate disposed on the upper electrode and the insulator, wherein a closed inner space is defined between the electret and the upper electrode and the spacer, wherein when the electric energy generator device receives the emitted ultrasonic-wave, a pressure in the inner space changes, to change a spacing between the electret and the upper electrode to generate an electric energy.

In one embodiment, the electric energy generator device comprises: a lower substrate; a lower electrode on the lower substrate; a spacer disposed on the lower substrate so as to surround the lower electrode; an electret disposed on the spacer to be spaced from the lower electrode; an upper electrode disposed on the electret; an insulator disposed on the spacer so as to surround the upper electrode and the electret; and an upper substrate disposed on the upper electrode and the insulator, wherein a closed inner space is defined between the electret and the lower electrode and the spacer, wherein when the electric energy generator device receives the emitted ultrasonic-wave, a pressure in the inner space changes, to change a spacing between the electret and the lower electrode to generate an electric energy.

In one embodiment, the system further comprises a load electrically coupled to the lower electrode and the upper electrode.

In one embodiment, the system further comprises a rectifier diode electrically coupled to and between the lower electrode and the load and/or between the upper electrode and the load.

In one embodiment, the electric energy generator device comprises: a lower substrate having a coil buried therein; an electrode on the lower substrate; a first friction-charged member on the electrode; a spacer disposed on the lower substrate so as to surround the electrode and the first friction-charged member; a second friction-charged member disposed on the spacer to be spaced from the first friction-charged member, wherein the second friction-charged member repeatedly contacts or is separated from the first friction-charged member; and an upper substrate on the second friction-charged member, wherein the upper substrate is magnetic, wherein a closed inner space is defined between the first friction-charged member and the second friction-charged member and the spacer, wherein when the electric energy generator device receives the emitted ultrasonic-wave, a pressure in the inner space changes, to deform the second friction-charged member to generate a first electric energy via a triboelectric effect between the first and second friction-charged members and a second electric energy via an electromagnetic induction between the upper and lower substrates.

In one embodiment, the electric energy generator device comprises: a lower substrate having a coil buried therein; an electrode on the lower substrate; a first electret on the electrode; a spacer disposed on the lower substrate so as to surround the electrode and the first electret; a second electret disposed on the spacer to be spaced from the first electret, wherein the first and second electrets have opposite polarization directions to each other; and an upper substrate on the second electret, wherein the upper substrate is magnetic, wherein a closed inner space is defined between the first and second electrets and the spacer, wherein when the electric energy generator device receives the emitted ultrasonic-wave, a pressure in the inner space changes, to change a spacing between the first and second electrets, to generate a first electric energy via a potential difference using the first and second electrets, and a second electric energy via an electromagnetic induction between the upper and lower substrates.

In one embodiment, the electric energy generator device comprises: a lower substrate having a coil buried therein; a lower electrode on the lower substrate; a first friction-charged member on the lower electrode; a spacer disposed on the lower substrate so as to surround the first electrode and the first friction-charged member; a second friction-charged member disposed on the spacer to be spaced from the first friction-charged member, wherein the second friction-charged member repeatedly contacts or is separated from the first friction-charged member; an upper electrode on the second friction-charged member; an insulator disposed on the spacer so as to surround the upper electrode and the second friction-charged member; and an upper substrate on the upper electrode and the insulator, wherein the upper substrate is magnetic, wherein a closed inner space is defined between the first friction-charged member and the second friction-charged member and the spacer, wherein when the electric energy generator device receives the emitted ultrasonic-wave, a pressure in the inner space changes, to deform the second friction-charged member to generate a first electric energy via a triboelectric effect between the first and second friction-charged members and a second electric energy via an electromagnetic induction between the upper and lower substrates.

In one embodiment, the electric energy generator device comprises: a lower substrate having a coil buried therein; a lower electrode on the lower substrate; a first electret on the lower electrode; a spacer disposed on the lower substrate so as to surround the lower electrode and the first electret; a second electret disposed on the spacer to be spaced from the first electret, wherein the first and second electrets have opposite polarization directions to each other; an upper electrode on the second electret; an insulator disposed on the spacer so as to surround the upper electrode and the second electret; and an upper substrate on the upper electrode and the insulator, wherein the upper substrate is magnetic, wherein a closed inner space is defined between the first and second electrets and the spacer, wherein when the electric energy generator device receives the emitted ultrasonic-wave, a pressure in the inner space changes, to change a spacing between the first and second electrets, to generate a first electric energy via a potential difference using the first and second electrets, and a second electric energy via an electromagnetic induction between the upper and lower substrates.

In the present disclosure, the ultrasonic-wave may be applied from the outside of the body into the body to generate the electric energy and thus the need for a separate batter in the body may be removed, to achieve a constant power supply to the electric consuming device in the body.

Further, an installation position of the electric energy generator device is not limited to specific position in the body since the ultrasonic-wave is applied from the outside of the body into the body to generate the electric energy. Thus, the freedom of the installation position of the electric energy generator device in the body may be secured.

Furthermore, via an adjustment of the ultrasonic-wave frequency, the generated electric energy may be controlled.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTIONS

Figure 1:
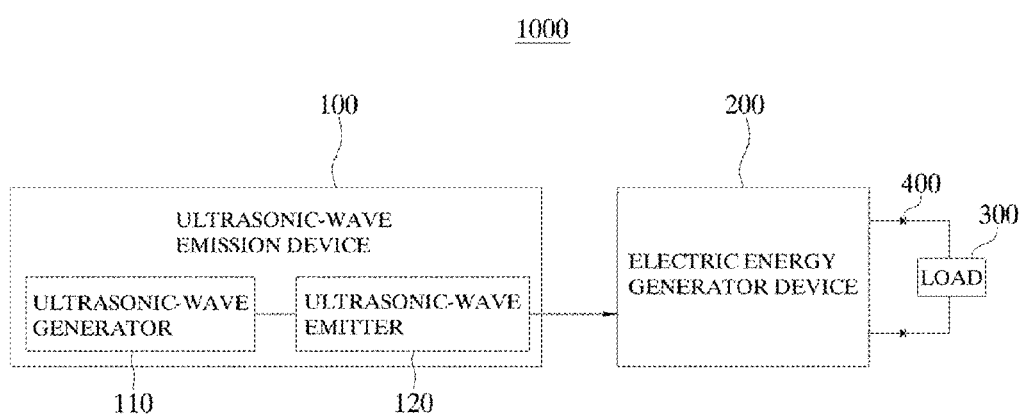
FIG. 1 shows a high-level diagram of an electric energy generator system using an ultrasonic wave in accordance with one embodiment of the present disclosure.

Examples of various embodiments are illustrated in the accompanying drawings and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

Example embodiments will be described in more detail with reference to the accompanying drawings. The present disclosure, however, may be embodied in various different forms, and should not be construed as being limited to only the illustrated embodiments herein. Rather, these embodiments are provided as examples so that this disclosure will be thorough and complete, and will fully convey the aspects and features of the present disclosure to those skilled in the art.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, s, operations, elements, and/or components, but do not preclude the presence or addition of one or more other features, integers, s, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure."

Hereinafter, embodiments of the present disclosure will be described in details with reference to attached drawings.

Figure 2:
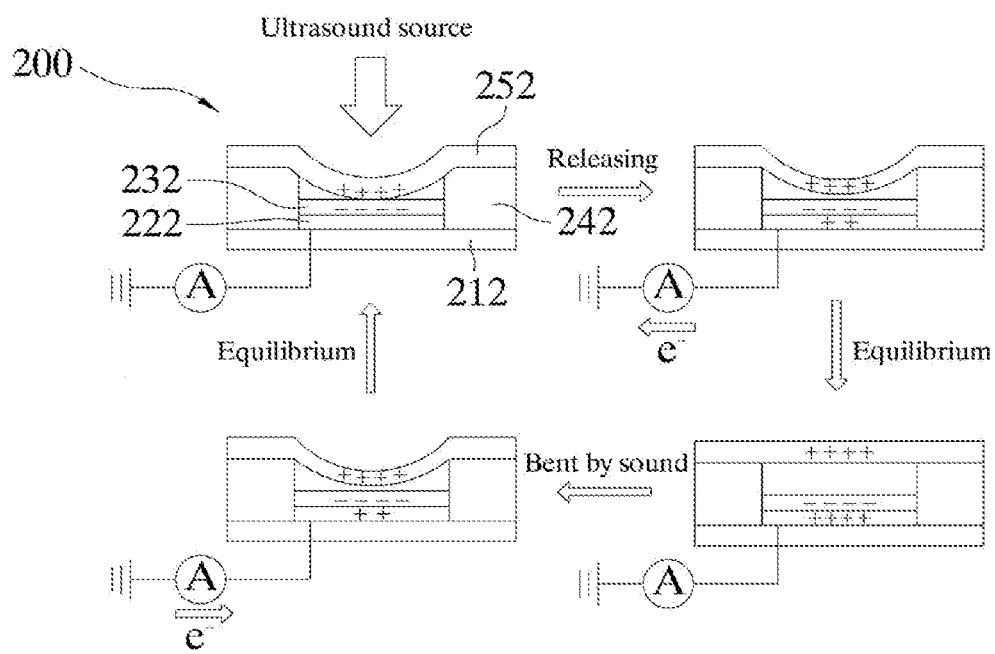
FIG. 2 illustrates a principle of electric energy generation for an electric energy generator device in accordance with one embodiment of the present disclosure.
Figure 3:
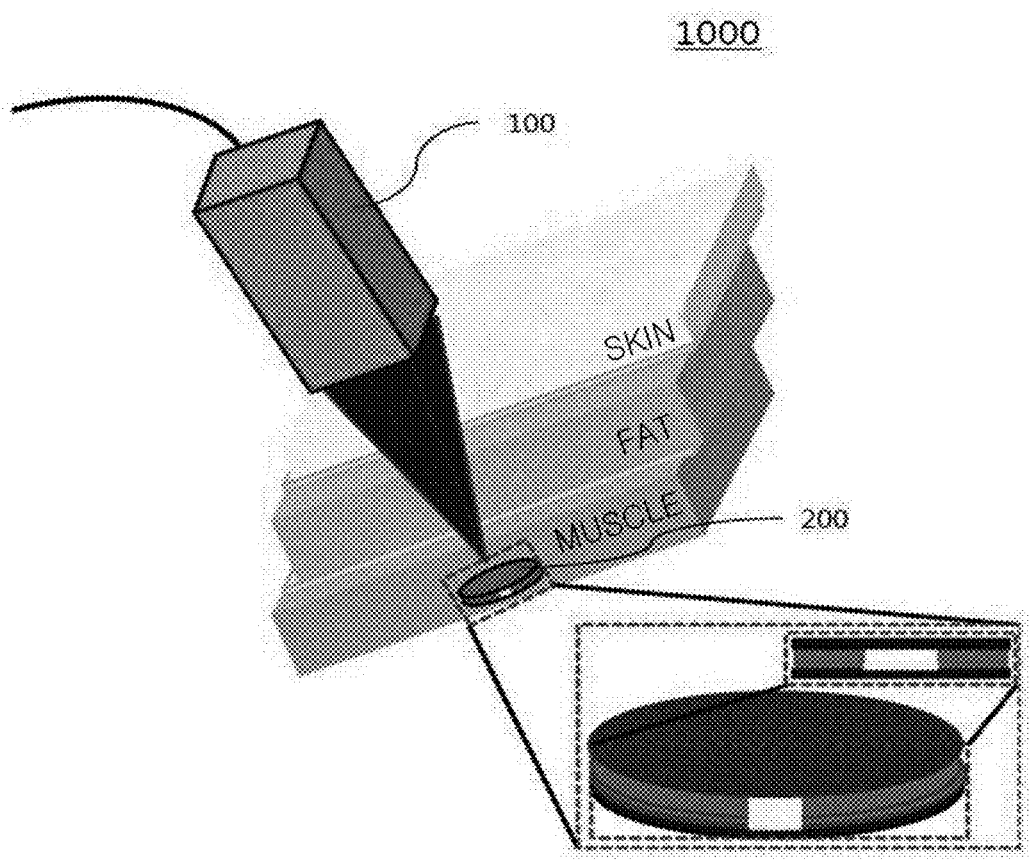
FIG. 3 shows a conceptional view for illustrating a state in which an electric energy generator system using an ultrasonic wave in accordance with one embodiment of the present disclosure is inserted into a body.

FIG. 1 shows a high-level diagram of an electric energy generator system using an ultrasonic wave in accordance with one embodiment of the present disclosure. FIG. 2 illustrates a principle of electric energy generation for an electric energy generator device in accordance with one embodiment of the present disclosure. FIG. 3 shows a conceptional view for illustrating a state in which an electric energy generator system using an ultrasonic wave in accordance with one embodiment of the present disclosure is inserted into a body.

Referring to FIG. 1 to FIG. 3, an electric energy generator system 1000 using an ultrasonic wave in accordance with one embodiment of the present disclosure may include an ultrasonic-wave emission device 100 and an electric energy generator device 200.

The ultrasonic-wave emission device 100 may generate an ultrasonic-wave and then emit the generated ultrasonic-wave. In one example, the ultrasonic-wave emission device 100 may include an ultrasonic-wave generator 110 configured to generate an ultrasonic-wave and an ultrasonic-wave emitter 120 configured to emit the ultrasonic-wave. In one example, the ultrasonic-wave generator 100 may generate the ultrasonic-wave with a frequency of about 20 kHz to 50 kHz and an intensity equal to or smaller than about 1 W/cm$^2$. Such an ultrasonic-wave emission device 100 may be portable. The ultrasonic-wave emission device 100 may have a controller (not shown) configured to adjust the frequency and intensity of the ultrasonic-wave and/or to activate or deactivate the emission of the ultrasonic-wave.

The electric energy generator device 200 may be configured to generate an electric energy on a receipt of the generated ultrasonic-wave from the ultrasonic-wave emission device 100. In one example, the electric energy generator device 200 may be hermetic to an external thereto, and may be insertable into the body and may be made of a material non-harmful to the body. In one example, when the ultrasonic-wave emission device 100 emits the ultrasonic-wave with the intensity larger than about 1 W/cm$^2$, the ultrasonic-wave may damage the body. Thus, in order to prevent this, the ultrasonic-wave with the intensity smaller than or equal to about 1 W/cm$^2$ may be applied to the ultrasonic-wave emission device 100 buried in the body.

In one example, the electric energy generator device 200 may include a substrate 212, an electrode 222, a first friction-charged member 232, a spacer 242 and a second friction-charged member 252. The present disclosure is not limited thereto. Various embodiments of the electric energy generator device 200 will be described individually later.

The substrate 212 may be made of a polymer non-harmful to the body. In one example, the substrate 212 may be made of Teflon. The present disclosure is not limited thereto.

The electrode 222 may be disposed on the substrate 212 at a middle region of the substrate 212. The electrode 222 may be made of a metal non-harmful to the body, for example, a gold (Au). The present disclosure is not limited thereto.

The first friction-charged member 232 may be disposed on the electrode 222. The first friction-charged member 232 may contact or be separated from the second friction-charged member 252 in a repeated manner. It may be preferable that the first and second friction-charged members 232 and 252 have different charging properties, which means that the first and second friction-charged members 232 and 252 are located at different positions in a triboelectric series.

The spacer 242 may be disposed on the substrate 212 so as to surround the electrode 222 and first friction-charged member 232. The spacer 242 may allow a physical separation between the first friction-charged member 232 and second friction-charged member 252. Thus, the spacer 242 and the first friction-charged member 232 and second friction-charged member 242 may define a closed space therebetween.

The second friction-charged member 252 may be disposed on the spacer 242 to be spaced from the first friction-charged member 232. The second friction-charged member 252 may contact or be separated from the first friction-charged member 232 in a repeated manner using the ultrasonic wave. In one example, the second friction-charged member 252 may be made of a non-metal material non-harmful to the body and with a good mechanical stability due to its repeated deformation. The ultrasonic wave energy from the ultrasonic-wave emission device 100 may change a pressure in the closed inner space between the first friction-charged member 232 and second friction-charged member 252 and the spacer 242. Such a change in the pressure may deform the second friction-charged member 252. The deformation of the second friction-charged member 252 may allow repetition of contact and separation between the second friction-charged member 252 and first friction-charged member 232. This repetition of contact and separation may generate a triboelectric energy. In one example, in order to increase the generated triboelectric energy, a contact area between the first friction-charged member 232 and second friction-charged member 252 may increase. In one example, in order to change a pressure in the closed inner space and thus allow repetition of contact and separation between the second friction-charged member 252 and first friction-charged member 232, the ultrasonic-wave applied to the electric energy generator device 200 may preferably a frequency of about 20 kHz to 50 kHz.

A spacing between the second friction-charged member 252 and first friction-charged member 232 may be configured to allow the repetition of contact and separation between the second friction-charged member 252 and first friction-charged member 232 when the second friction-charged member 252 is deformed. In one example, it may be preferable that the first and second friction-charged members 232 and 252 have different charging properties, which means that the first and second friction-charged members 232 and 252 are located at different positions in a triboelectric series. The larger difference may lead to a larger triboelectric amount.

The electric energy generator device 200 may be insertable into the body, and, thus, may be made of a material non-harmful to the body. Thus, the electric energy generator device 200 may include the components, namely, the substrate 212, spacer 242 and second friction-charged member 252, all of which may contact a human body cell and be made of a material non-harmful to the body. Further, in order that the friction electric generated between the first friction-charged member 232 and second friction-charged member 252 does not affect the body, each of the substrate 212, spacer 242 and second friction-charged member 252 may be made of a non-conductive material. In one example, the substrate 212 may be made of PDMS, Ecoflex, PEN, silicon, etc. and the spacer 242 may be made of Kapton, acrylic, etc.

Further, each of the substrate 212, first friction-charged member 232, spacer 242 and second friction-charged member 252 may be made of a material with a sufficiently high Young's modulus.

The electric energy generator system 1000 using an ultrasonic wave in accordance with one embodiment of the present disclosure may further include a load 300 electrically coupled to the electrode 222. In one example, the load 300 may be embodied as an electric or electronic module, or condenser. To be specific, the load 300 may be embodied as a cardiac pacemaker. The present disclosure is not limited thereto. Further, the electric energy generator system 1000 using an ultrasonic wave in accordance with one embodiment of the present disclosure may further a rectifier diode 400 electrically coupled to and between the electrode 222 and load 300. The rectifier diode 400 may act to allow the current between the electrode 222 and load 300 to flow only in a single direction to suppress the condenser 300 form be discharged. The load 300 and rectifier diode 400 may be contained in the electric energy generator device 200.

Figure 4A:
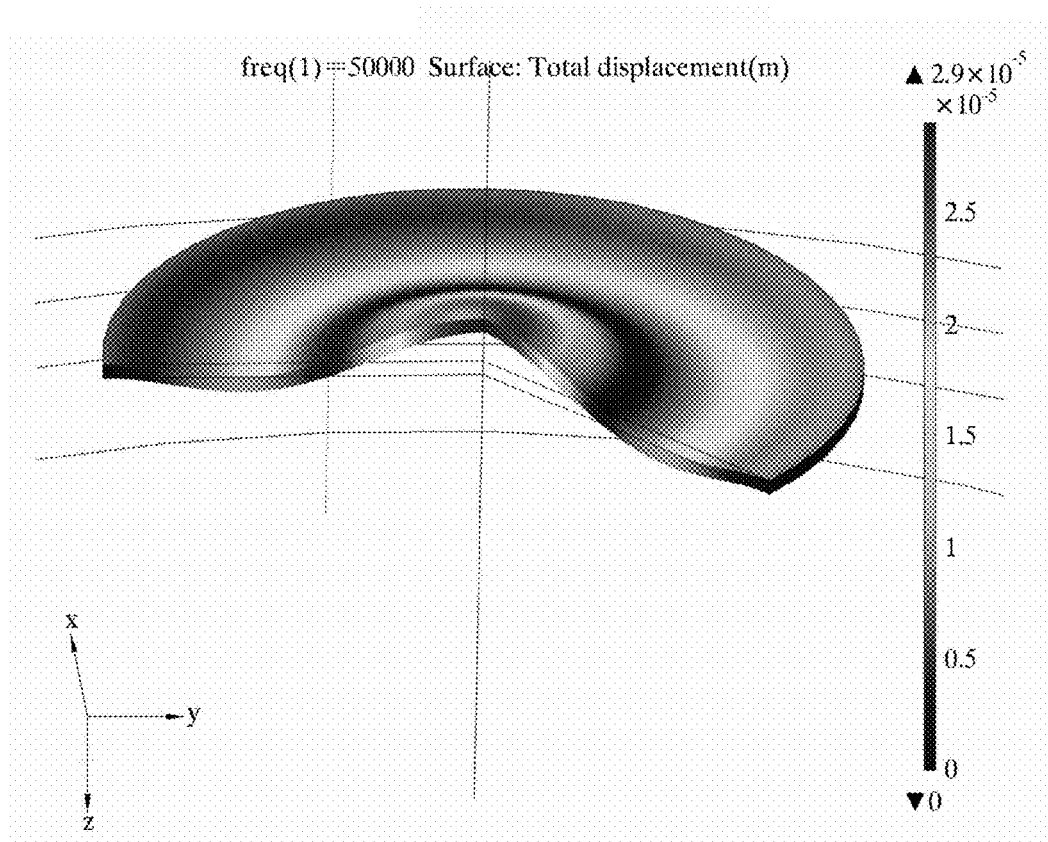
FIG. 4A shows a graph of measurement of deformation of a second friction-charged member due to an ultrasonic wave energy.

FIG. 4A shows a graph of measurement of deformation of a second friction-charged member due to an ultrasonic wave energy.

The deformation is measured using a COMSOL simulation.

Referring to FIG. 4A, it is confirmed that a central region with a radius of about 1 cm in the second friction-charged member may be deformed to be convex due to an ultrasonic wave energy applied thereto. This may be due to a pressure difference between the inner space and the outer space due to the ultrasonic-wave. The deformation of the second friction-charged member may allow the repetition of contact and separation between the second friction-charged member and first friction-charged member.

Figure 4B:
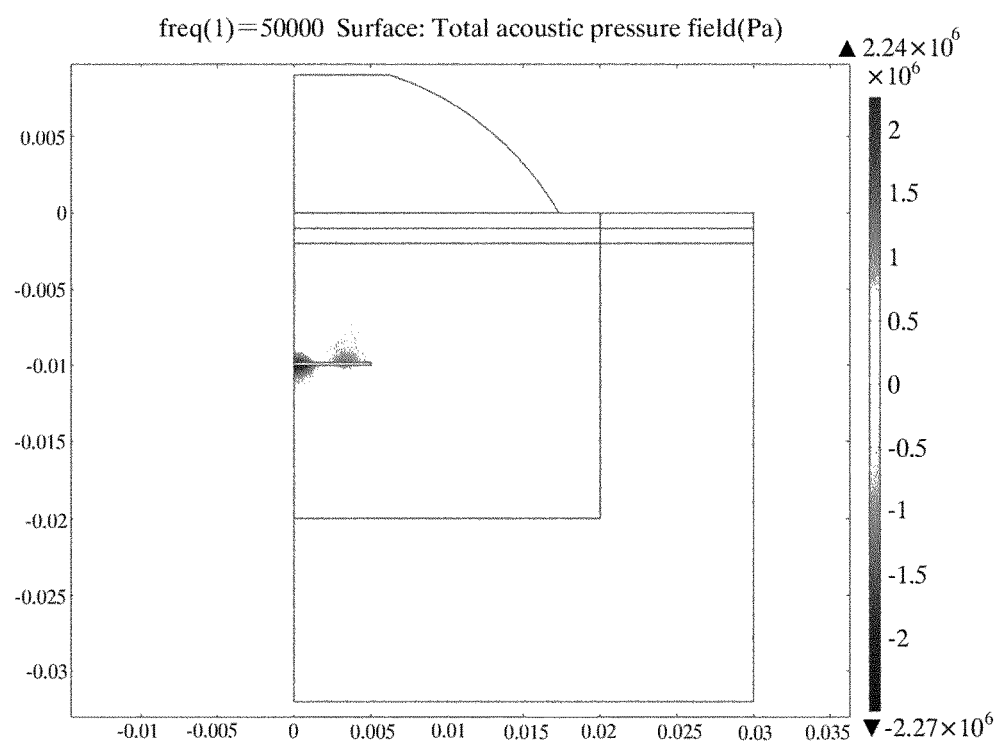
FIG. 4B and FIG. 4C show graphs pressure variations applied to a second friction-charged member due to an ultrasonic wave energy.
Figure 4C:
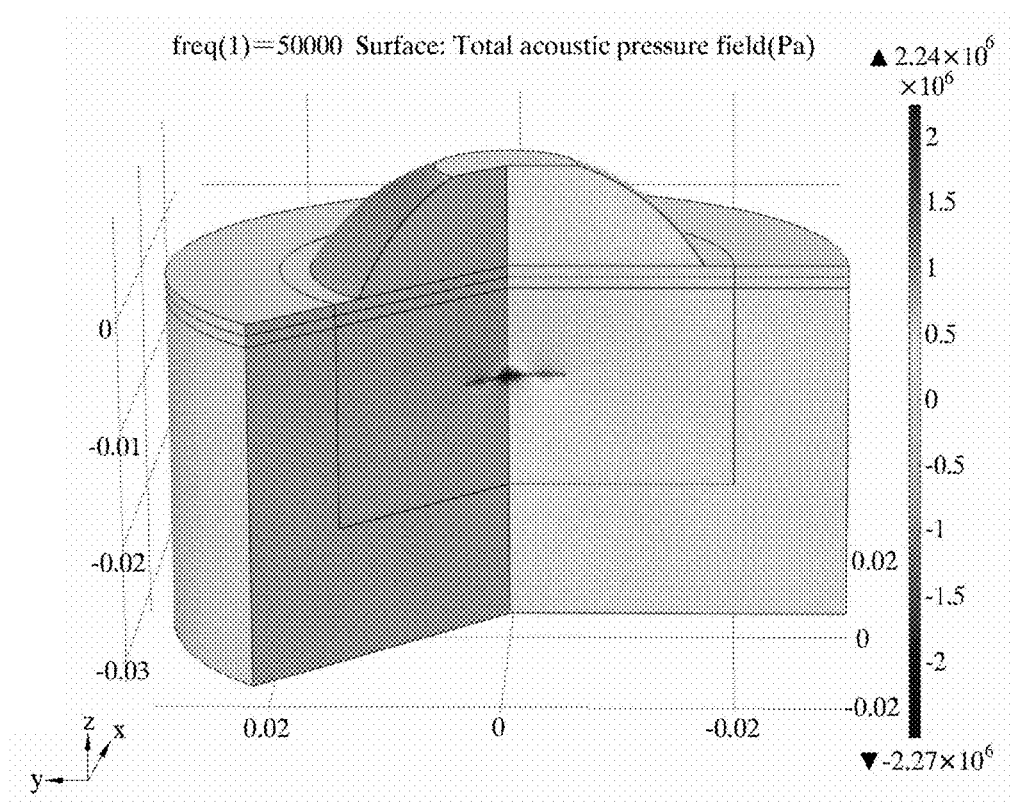

FIG. 4B and FIG. 4C show graphs pressure variations applied to a second friction-charged member due to an ultrasonic wave energy. When the frequency of the emitted ultrasonic-wave is 50 kHz, pressure variations applied to the second friction-charged member are measured using a COMSOL simulation.

Referring to FIG. 4B and FIG. 4C, it is confirmed that the central region of the second friction-charged member may have the greatest pressure difference. Such a difference in the pressure may allow the repetition of contact and separation between the second friction-charged member and first friction-charged member.

Figure 5:
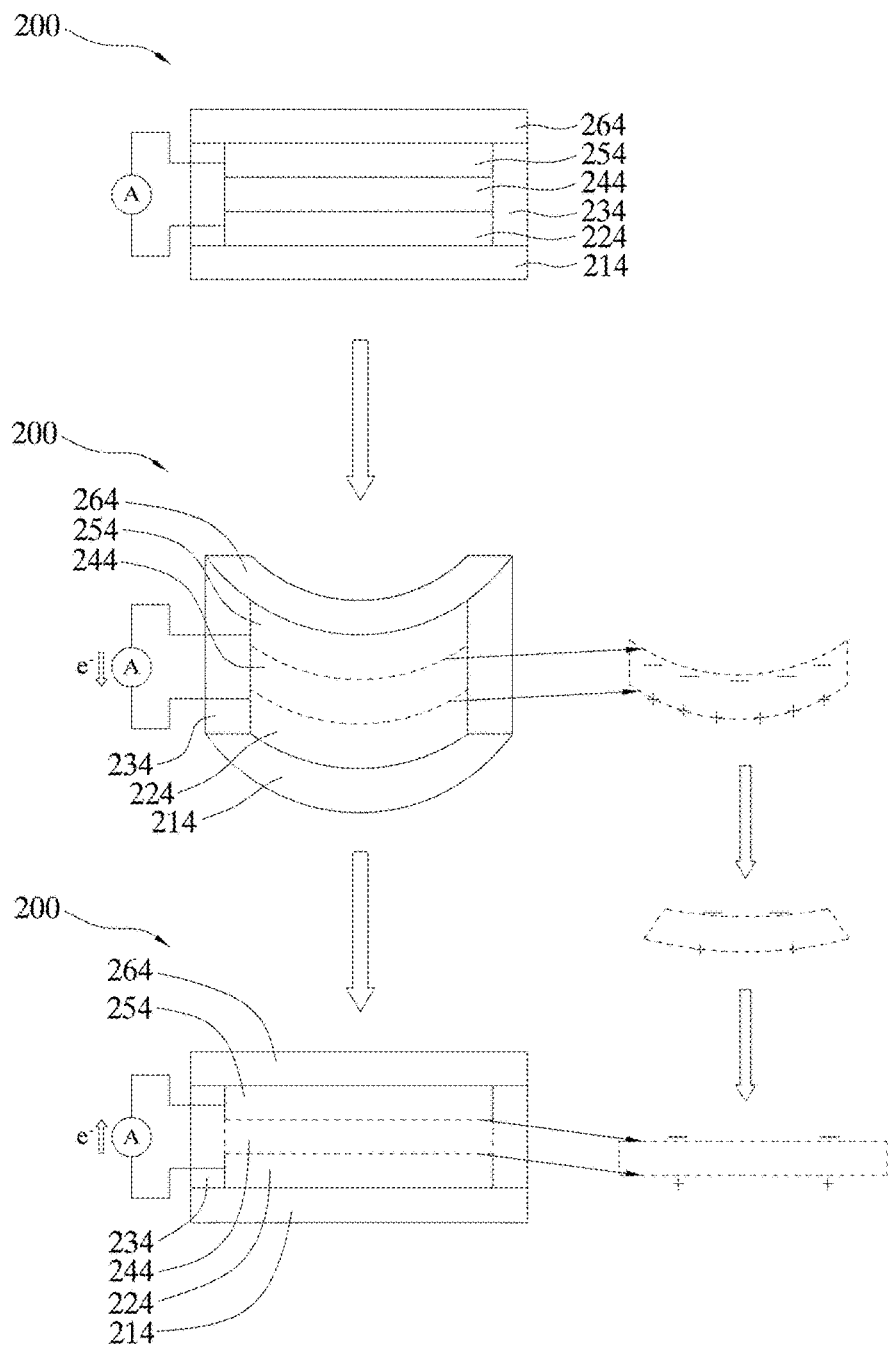
FIG. 5 shows a conceptional view for illustrating an electric energy generator device in accordance with another embodiment of the present disclosure.

FIG. 5 shows a conceptional view for illustrating an electric energy generator device in accordance with another embodiment of the present disclosure.

Referring to FIG. 5, an electric energy generator device 200 in accordance with another embodiment of the present disclosure may include a lower substrate 214, a lower electrode 224, a piezoelectric layer 244, an upper electrode 254, an insulator 234 and an upper substrate 264.

The lower substrate 214 may be made of a non-conductive polymer non-harmful to the body. In one example, the lower substrate 214 may be made of Teflon. The present disclosure is not limited thereto.

The lower electrode 224 may be disposed on the lower substrate 214 at a middle region of the lower substrate 214. The lower electrode 224 may be made of a metal non-harmful to the body, for example, gold (Au). The present disclosure is not limited thereto.

The piezoelectric layer 244 may be disposed on the lower electrode 224 and may be made of a piezoelectric material. In one example, the piezoelectric material may include $ZnSnO_3$, $BaTiO_3$, $BiFeO_3$, etc. The present disclosure is not limited thereto.

The upper electrode 254 may be disposed on the piezoelectric layer 244, and may be made of a metal non-harmful to the body, for example, gold (Au). The present disclosure is not limited thereto.

The insulator 234 may be disposed on the lower substrate 214 so as to surround the lower electrode 224, piezoelectric layer 244 and upper electrode 254.

The upper substrate 264 may be disposed on the upper electrode 254 and insulator 234. Thus, the inner space defined between the lower substrate 214, insulator 254 and upper substrate 264 may be closed. The electric energy generator device 200 may be insertable into the body, and, thus, may be made of a material non-harmful to the body. Thus, the electric energy generator device 200 may include the lower electrode 224, insulator 234 and upper substrate 264 which may contact a human body cell and may be made of a material non-harmful to the body.

In one example, each of the lower substrate 214, lower electrode 224, piezoelectric layer 244, upper electrode 254, insulator 234 and upper substrate 264 may be deformed repeatedly, and, thus, may be made of a material with a good mechanical stability.

The ultrasonic-wave emission device 100 may emit the generated ultrasonic-wave to the electric energy generator device 200 in accordance with another embodiment of the present disclosure, which in turn may vibrate and thus deform. Such a deformation may generate a potential difference in the piezoelectric layer 244, which in turn, lead to an electric energy.

A load 300 may be electrically coupled to the lower electrode 224 and upper electrode 254 of the electric energy generator device 200 to consume the generated electric energy from the electric energy generator device 200. Further, a rectifier diode 400 may be electrically coupled to and between the lower electrode 224 and load 300 and/or between the upper electrode 254 and load 300. The load 300 and rectifier diode 400 may be same as described above in a configuration.

Figure 6A:
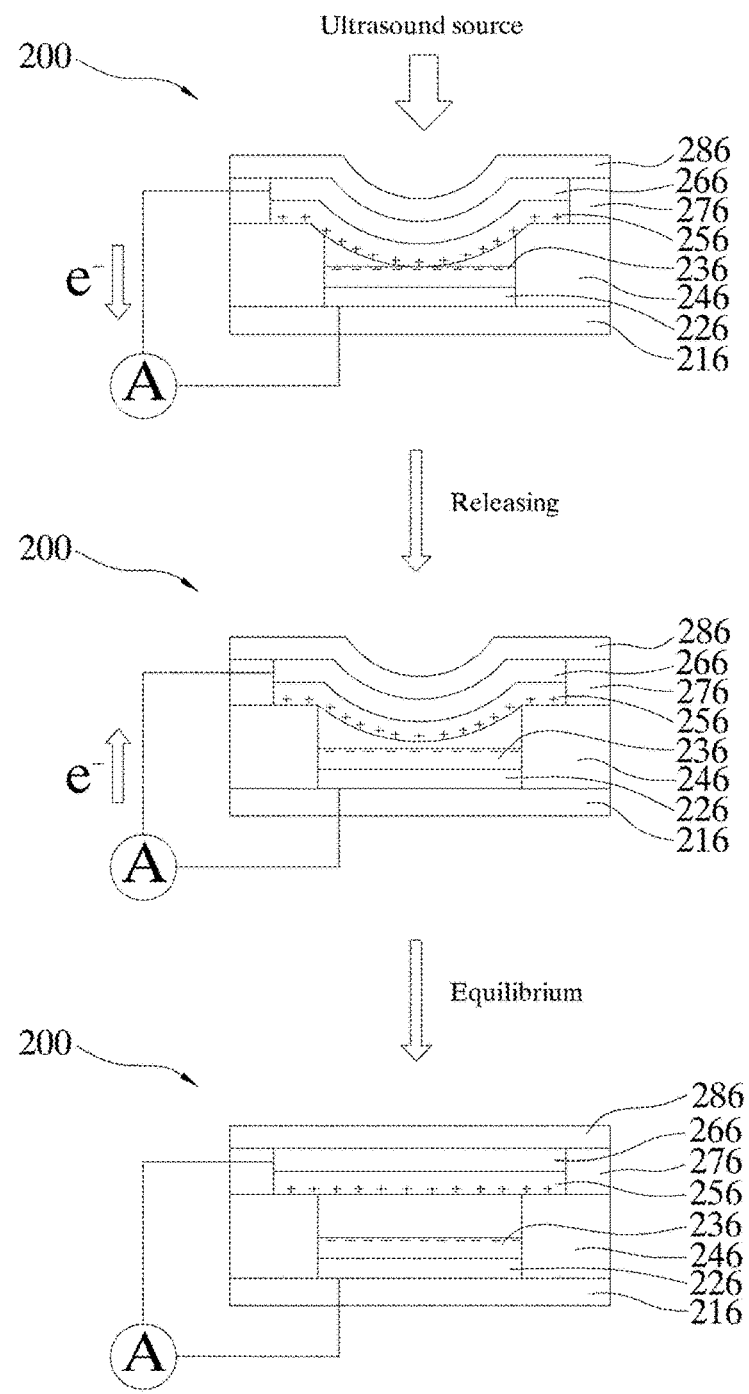
FIG. 6A to FIG. 6C show conceptional views for illustrating an electric energy generator device in accordance with still another embodiment of the present disclosure.
Figure 6B:
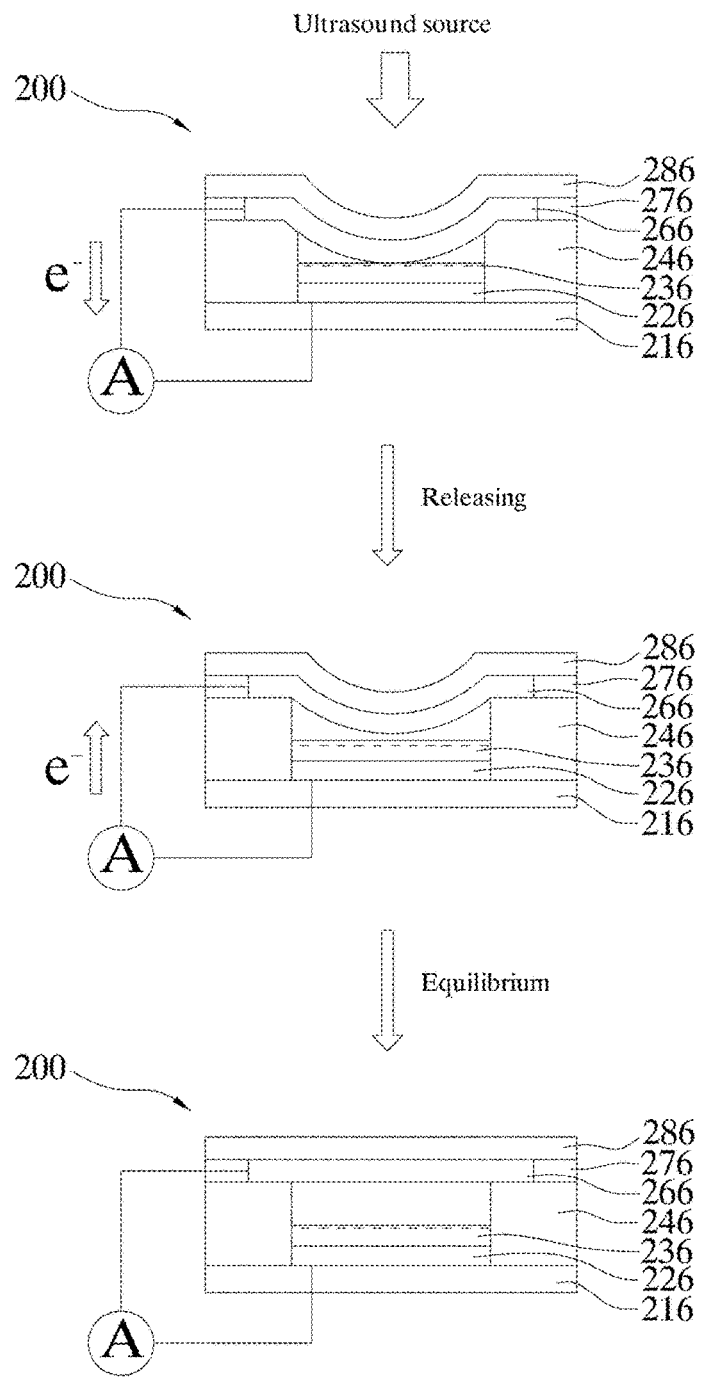
Figure 6C:
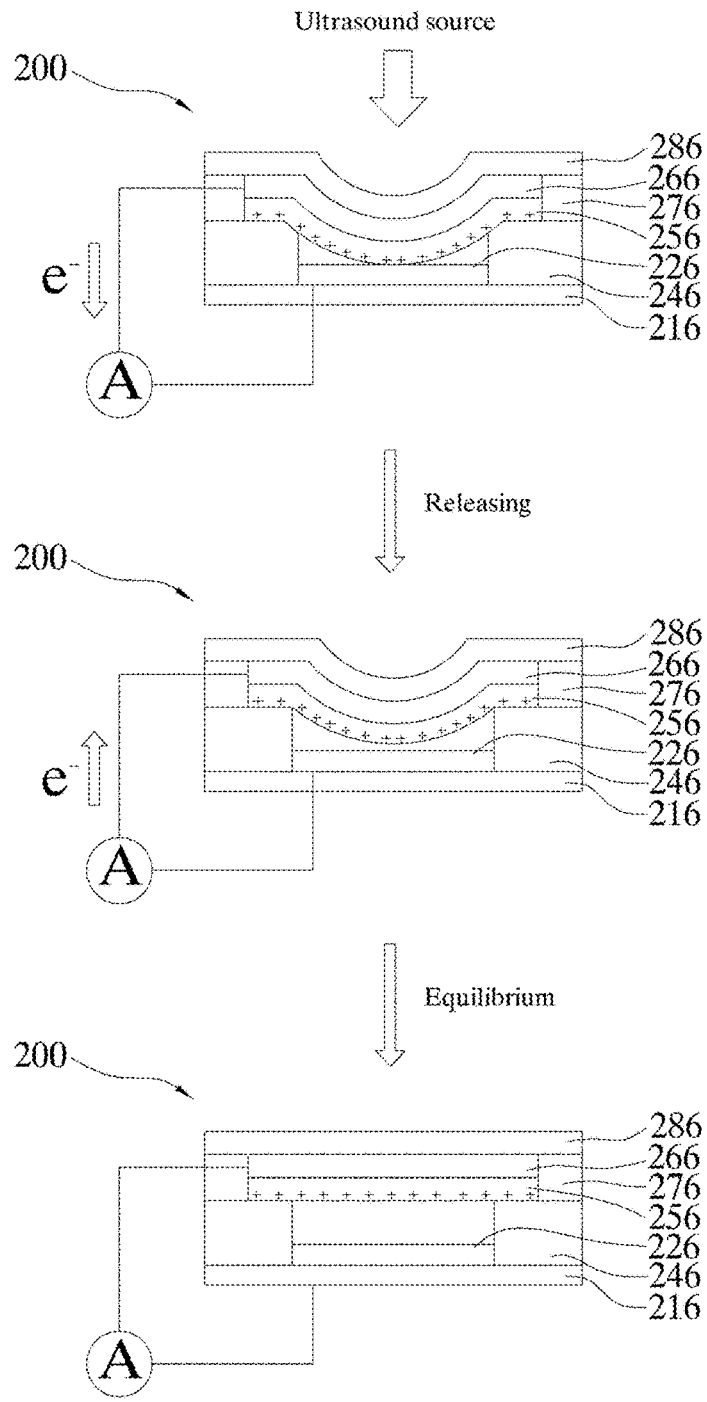

FIG. 6A to FIG. 6C show conceptional views for illustrating an electric energy generator device in accordance with still another embodiment of the present disclosure.

Referring to FIG. 6A, the electric energy generator device 200 in accordance with still another embodiment of the present disclosure may include a lower substrate 216, a lower electrode 226, a first electret 236, a spacer 246, a second electret 256, an upper electrode 266, an insulator 276 and an upper substrate 286.

The lower substrate 216 may be made of a non-conductive polymer non-harmful to the body. In one example, the lower substrate 216 may be made of Teflon. The present disclosure is not limited thereto.

The lower electrode 226 may be disposed on the lower substrate 216 in a middle region of the lower substrate 216. The lower electrode 226 may be made of a metal non-harmful to the body, for example, gold (Au). The present disclosure is not limited thereto.

The first electret 236 may be disposed on the lower electrode 226. The electret may refer to a dielectric with a quasi-permanent polarization. The first electret 236 may be made of pvdf, p(vdf-trfe), ptfe, pdms, etc. The present disclosure is not limited thereto.

The spacer 246 may be disposed on the lower substrate 216 so as to surround the lower electrode 226 and first electret 236. The spacer 246 may allow a separation between the first electret 236 and second electret 256 and thus the inner space defined between the first electret 236 and second electret 256 and the spacer 246 may be closed.

The second electret 256 may be disposed on the first insulator 246 to be spaced from the first electret 236. The second electret 256 may have a polarization direction opposite that of the first electret 236. In one example, the first electret 236 and second electret 256 may be configured such that the first electret 236 and second electret 256 have mutually-facing ends which are oppositely charged respectively. In one example, the second electret 256 may be made of pvdf, p(vdf-trfe), ptfe, pdms, etc. The present disclosure is not limited thereto.

The upper electrode 266 may be disposed on the second electret 256. The upper electrode 266 may be made of a metal non-harmful to the body, for example, gold (Au). The present disclosure is not limited thereto.

The insulator 276 may be disposed on the spacer 246 to surround the second electret 256 and upper electrode 266.

The upper substrate 286 may be disposed on the upper electrode 266 and insulator 276. The inner space defined between the lower substrate 216, spacer 246, insulator 276 and upper substrate 286 may be closed.

In operation, the ultrasonic-wave emission device 100 may emit the ultrasonic wave energy to the electric energy generator device 200. Thus, the pressure in the inner space between the first electret 236 and second electret 256 may change. This change in the pressure may deform the second electret 256. When the second electret 256 has the deformation, the spacing between the second electret 256 and first electret 236 may reduce. The spacing reduction may allow the contact between the second electret 256 and first electret 236.

When the spacing between the second electret 256 and first electret 236 reduces, a potential difference between the second electret 256 and first electret 236 may change. Such a difference in the potential may lead to an electric current. Further, the spacing reduction may allow the contact between the second electret 256 and first electret 236. This contact may change a potential difference between the second electret 256 and first electret 236. Such a difference in the potential may lead to an electric current. Thus, when the second electret 256 and first electret 236 contact each other, the triboelectric electric energy may be added to the electric energy resulting from the potential difference.

A load 300 may be electrically coupled to the lower electrode 216 and upper electrode 266 of the electric energy generator device 200 to consume the generated electric energy from the electric energy generator device 200. Further, a rectifier diode 400 may be electrically coupled to and between the lower electrode 216 and load 300 and/or between the upper electrode 266 and load 300. The load 300 and rectifier diode 400 may be same as described above in a configuration.

The above embodiment has both the first electret 236 and second electret 256. The present disclosure is not limited thereto. FIG. 6B to FIG. 6C show embodiments free of the second electret 256 or first electret 236 respectively. The embodiment of FIG. 6B free of the second electret 256 may be substantially the same as the embodiment of FIG. 6A in a configuration except for the lack of the second electret 256. The embodiment of FIG. 6C free of the first electret 236 may be substantially the same as the embodiment of FIG. 6A in a configuration except for the lack of the first electret 236.

FIG. 7A to FIG. 7D show conceptional views for illustrating an electric energy generator device in accordance with further still another embodiment of the present disclosure.

Figure 7A:
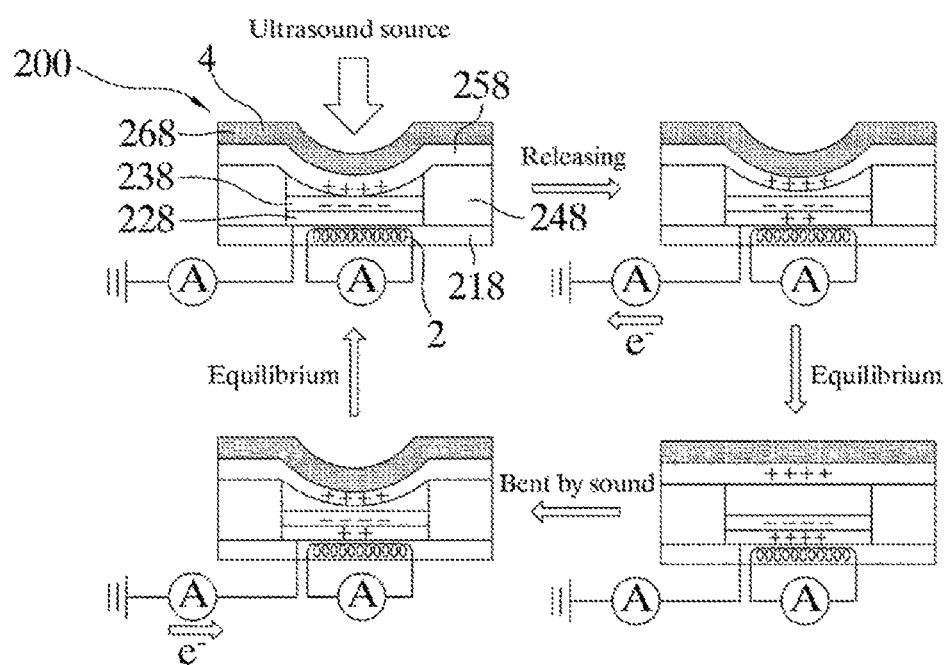
FIG. 7A to FIG. 7D show conceptional views for illustrating an electric energy generator device in accordance with further still another embodiment of the present disclosure.

Referring to FIG. 7A, the electric energy generator device 200 in accordance with further still another embodiment of the present disclosure may include a lower substrate 218, a lower electrode 228, a first friction-charged member 238, a spacer 248, a second friction-charged member 258 and an upper substrate 268.

The lower substrate 214 may be made of a polymer non-harmful to the body. In one example, the lower substrate 214 may be made of Teflon. The present disclosure is not limited thereto. In one example, in the lower substrate 214, a coil 2 may be buried.

The lower electrode 228 may be disposed on the lower substrate 218 in a middle region of the lower substrate 218. The lower electrode 228 may be made of a metal non-harmful to the body, for example, gold (Au). The present disclosure is not limited thereto.

The first friction-charged member 238 may be disposed on the lower electrode 228. The first friction-charged member 238 may contact and be separated from the second friction-charged member 258 repeatedly. It may be preferable that the first and second friction-charged members 238 and 258 have different charging properties, which means that the first and second friction-charged members 238 and 258 are located at different positions in a triboelectric series.

The spacer 248 may be disposed on the lower substrate 218 so as to surround the lower electrode 228 and first friction-charged member 238. The spacer 248 may allow the separation between the first friction-charged member 238 and second friction-charged member 258. The inner space defined between the first friction-charged member 238 and second friction-charged member 258 and the spacer 248 may be closed.

The second friction-charged member 258 may be disposed on the spacer 248 to be spaced from the first friction-charged member 238. The second friction-charged member 258 may contact and be separated from the first friction-charged member 238 repeatedly. In one example, since the second friction-charged member 258 has repetitions of the deformations, the second friction-charged member 258 may be made of a material with a good mechanical stability. The second friction-charged member 258 may be made of a non-metal non-harmful to the body.

In operation, the ultrasonic-wave emission device 100 may emit an ultrasonic wave energy to the device 200. Thus, a pressure in the inner space between the first friction-charged member 238 and second friction-charged member 258 may change. Such a change in the pressure may allow the second friction-charged member 258 to have deformation. When the second friction-charged member 258 has the deformation, the second friction-charged member 258 and first friction-charged member 238 may contact and be separated from each other to lead to the triboelectric energy. In one example, it may be preferable that the first and second friction-charged members 238 and 258 have different charging properties, which means that the first and second friction-charged members 238 and 258 are located at different positions in a triboelectric series. The larger difference may lead to a larger triboelectric amount.

The electric energy generator device 200 may be insertable into the body, and, thus, may be made of a material non-harmful to the body. Thus, the electric energy generator device 200 may include the lower substrate 218, spacer 248, second friction-charged member 258, and upper substrate 268, all of which may contact a human body cell and be made of a material non-harmful to the body.

The upper substrate 268 may be disposed on the second friction-charged member 258 and may be made of a magnetic material. In one example, the upper substrate 268 may have magnetic powers of fine particles dispersed therein. In an alternative, the upper substrate 268 may form a thin film magnet.

When the second friction-charged member 258 has the deformation and thus the second friction-charged member 258 contacts the first friction-charged member 238, the spacing between the magnetic upper substrate 268 and the lower substrate 218 having the coil buried therein may be smaller. To the contrary, when the second friction-charged member 258 is separated from the first friction-charged member 238, the spacing between the magnetic upper substrate 268 and the lower substrate 218 having the coil buried therein may be larger. This spacing variation between the magnetic upper substrate 268 and the lower substrate 218 having the coil buried therein may lead to the current flow in the coil via an electromagnetic induction. Thus, the electric energy generator device 200 in this embodiment may generate the first electric energy via the electromagnetic induction and, at the same time, generate the second electric energy via the triboelectric effect.

In order to consume the first generated electric energy, the electric energy generator device 200 may include a first load 300 electrically coupled across the coil 2 buried in the lower substrate 218. Further, in order to consume the second generated electric energy, the electric energy generator device 200 may include a second load 300 electrically coupled to the lower electrode 218. Alternatively, in order to consume the first and second generated electric energies, the electric energy generator device 200 may include a single load 300 electrically coupled across the coil 2 buried in the lower substrate 218 and electrically coupled to the lower electrode 228. In one example, the load 300 may be embodied as an electric or electronic module, or condenser. To be specific, the load 300 may be embodied as a cardiac pacemaker. The present disclosure is not limited thereto.

Figure 7B:
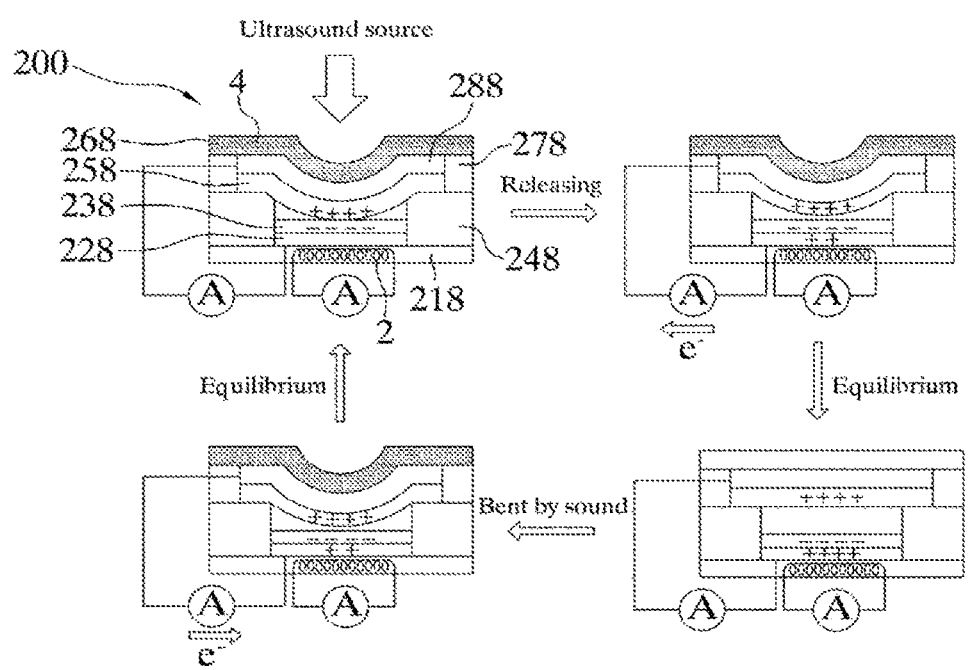

FIG. 7B shows an embodiment of a variation of FIG. 7A wherein the electric energy generator device 200 of FIG. 7B further comprises an upper electrode 288 and insulator 278. Referring to 7B, the upper electrode 288 may be disposed between the second friction-charged member 258 and upper substrate 268. The insulator 278 may be disposed on the spacer 248 so as to surround the second friction-charged member 258 and upper electrode 288.

A load 300 may be electrically coupled to the lower electrode 228 and upper electrode 288 of the electric energy generator device 200 to consume the generated electric energy from the electric energy generator device 200. Further, a rectifier diode 400 may be electrically coupled to and between the lower electrode 228 and load 300 and/or between the upper electrode 288 and load 300. The load 300 and rectifier diode 400 may be same as described above in a configuration.

Figure 7C:
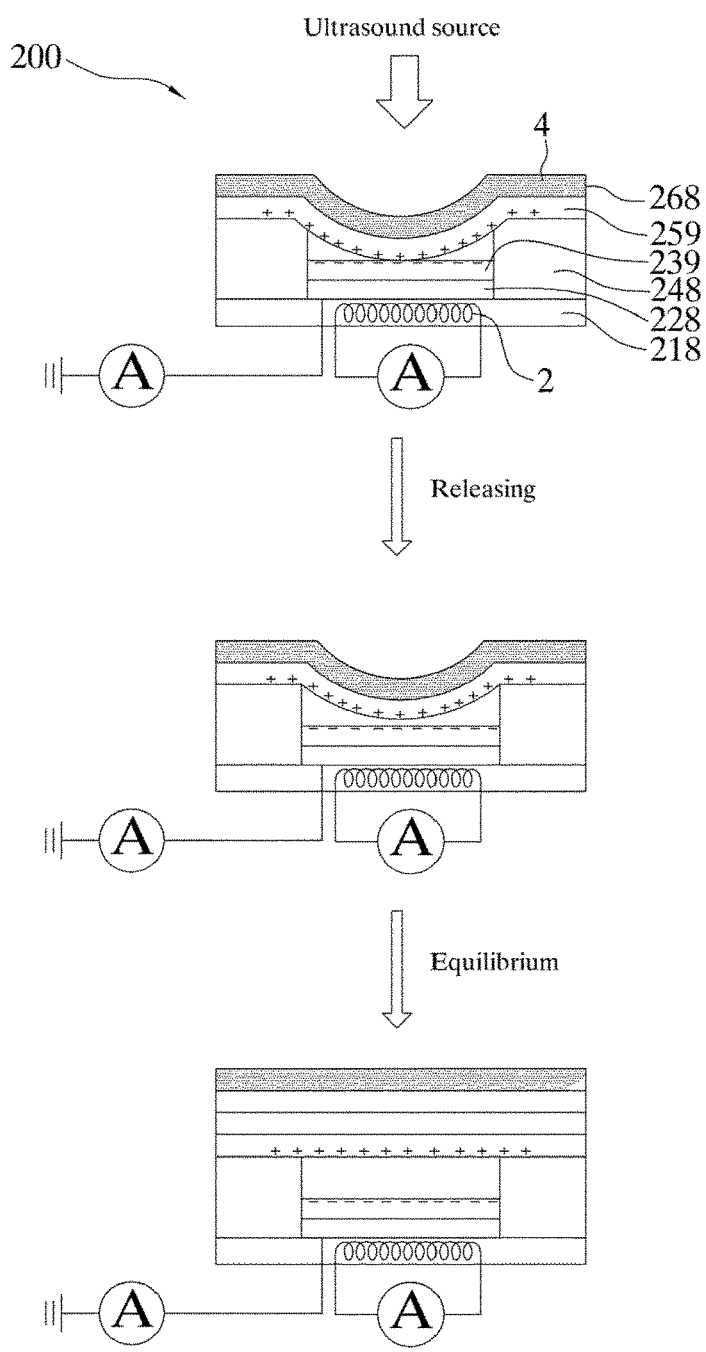

FIG. 7C shows an embodiment of a variation of FIG. 7A wherein the first friction-charged member 228 and second friction-charged member 258 in FIG. 7A are replaced with a first electret 239 and a second electret 259 respectively.

In operation, the ultrasonic-wave emission device 100 may emit the ultrasonic wave energy to the electric energy generator device 200. Thus, the pressure in the inner space between the first electret 239 and second electret 259 may change. This change in the pressure may deform the second electret 259. When the second electret 259 has the deformation, the spacing between the second electret 259 and first electret 239 may reduce. The spacing reduction may allow the contact between the second electret 259 and first electret 239.

When the spacing between the second electret 256 and first electret 236 reduces, a potential difference between the second electret 259 and first electret 239 may change. Such a difference in the potential may lead to an electric current. Further, the spacing variation between the magnetic upper substrate 268 and the lower substrate 218 having the coil buried therein may lead to the current flow in the coil via an electromagnetic induction. Thus, the electric energy generator device 200 in this embodiment may generate the first electric energy via the electromagnetic induction and, at the same time, generate the second electric energy via the potential difference.

In order to consume the first generated electric energy, the electric energy generator device 200 may include a first load 300 electrically coupled across the coil 2 buried in the lower substrate 218. Further, in order to consume the second generated electric energy, the electric energy generator device 200 may include a second load 300 electrically coupled to the lower electrode 218. Alternatively, in order to consume the first and second generated electric energies, the electric energy generator device 200 may include a single load 300 electrically coupled across the coil 2 buried in the lower substrate 218 and electrically coupled to the lower electrode 228. In one example, the load 300 may be embodied as an electric or electronic module, or condenser. To be specific, the load 300 may be embodied as a cardiac pacemaker. The present disclosure is not limited thereto.

Figure 7D:
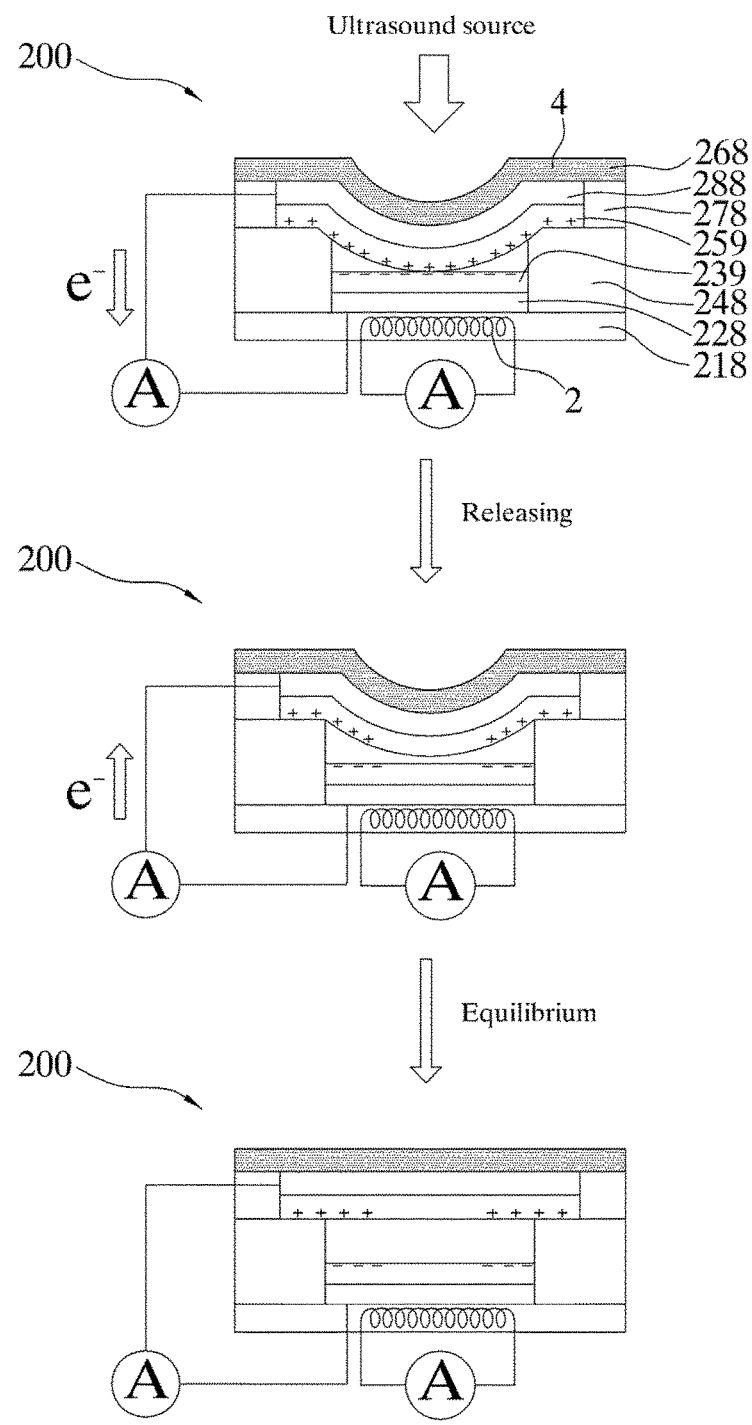

FIG. 7D shows an embodiment of a variation of FIG. 7C wherein the electric energy generator device 200 of FIG. 7D further comprises an upper electrode 288 and insulator 278. Except for the addition of the upper electrode 288 and insulator 278, the embodiment of FIG. 7D may be substantially the same the embodiment of FIG. 7C in a configuration.

Figure 8:
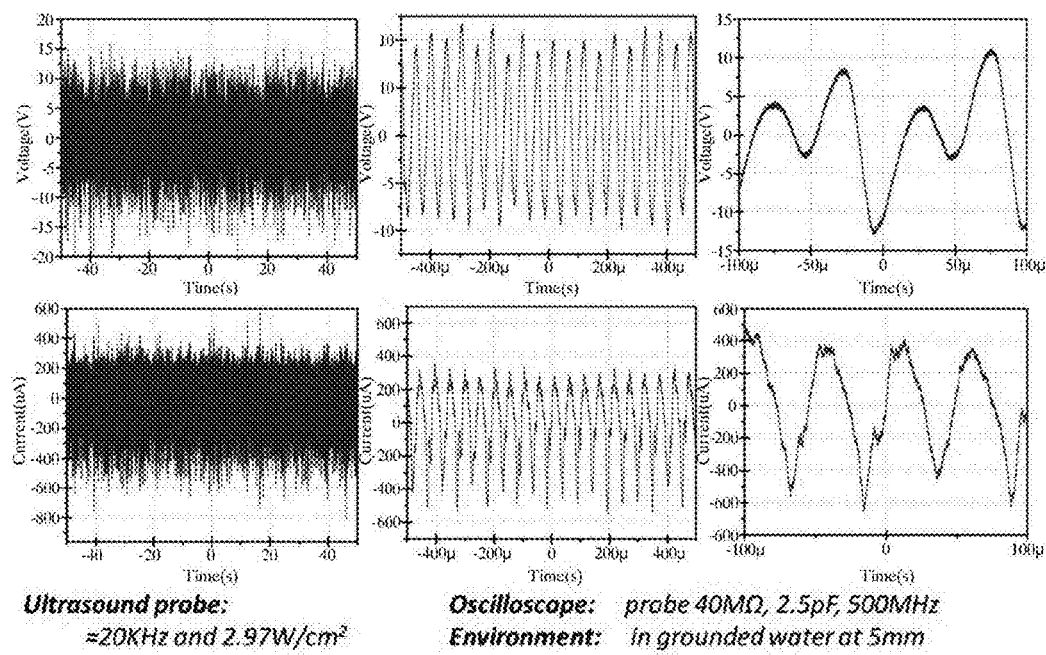
FIG. 8 illustrates one example of an electrical output performance achieved by an electric energy generator system using an ultrasonic wave in accordance with one embodiment of the present disclosure.

FIG. 8 illustrates one example of an electrical output performance achieved by an electric energy generator system using an ultrasonic wave in accordance with one embodiment of the present disclosure. The example of FIG. 8 shows output voltages and currents from the present electric energy generator system when an ultrasonic wave with a 20 kHz frequency is applied to the electric energy generator device 200 as shown in FIG. 2, generating a triboelectric energy in a water wherein the spacing between the first and second friction-charged members is about 5 mm.

The above description is not to be taken in a limiting sense, but is made merely for the purpose of describing the general principles of exemplary embodiments, and many additional embodiments of this disclosure are possible. It is understood that no limitation of the scope of the disclosure is thereby intended. The scope of the disclosure should be determined with reference to the Claims. Reference throughout this specification to "one embodiment," "an embodiment," or similar language means that a particular feature, structure, or characteristic that is described in connection with the embodiment is included in at least one embodiment of the present disclosure. Thus, appearances of the phrases "in one embodiment," "in an embodiment," and similar language throughout this specification may, but do not necessarily, all refer to the same embodiment.

What is claimed is:

1. An electric energy generator system comprising:
   an ultrasonic-wave emission device configured to generate an ultrasonic-wave and emit the ultrasonic-wave; and
   an electric energy generator device configured to generate an electric energy upon a receipt of the emitted ultrasonic-wave,
   wherein the electric energy generator device comprises:
   a substrate;
   an electrode on the substrate;
   a first friction-charged member on the electrode;
   a spacer disposed on the substrate and configured to surround the electrode and the first friction-charged member; and
   a second friction-charged member disposed on the spacer to be spaced from the first friction-charged member,
   wherein the second friction-charged member repeatedly contacts or is separated from the first friction-charged member, and
   wherein a closed inner space is defined between the first friction-charged member and the second friction-charged member and the spacer.

2. The system of claim 1, wherein the ultrasonic-wave emission device comprises:
   an ultrasonic-wave generator configured to generate the ultrasonic-wave; and
   ultrasonic-wave emitter configured to emit the generated ultrasonic-wave.

3. The system of claim 1, wherein the electric energy generator device has a closed inner space defined therein and the electric energy generator device is insertable into a living body.

4. The system of claim 1,
wherein when the electric energy generator device receives the emitted ultrasonic-wave, a pressure in the inner space changes, to allow deformation of the second friction-charged member and thus repetitions of the contact and separation between the first and second friction-charged members, to generate a triboelectric energy.

5. The system of claim 1, further comprising a load electrically coupled to the electrode.

6. The system of claim 5, wherein the load includes an electric device, an electronic device or a condenser.

7. The system of claim 5, further comprising a rectifier diode electrically coupled to and between the electrode and the load.

8. The system of claim 1, wherein the ultrasonic-wave has an intensity smaller than or equal to 1 W/cm$^2$.

9. The system of claim 1, wherein the ultrasonic-wave has a frequency of 20 kHz to 50 kHz.

10. The system of claim 1, wherein the substrate is a lower substrate having a coil buried therein,
wherein the electric energy generator device further comprises an upper substrate, which is magnetic, disposed on the second friction-charged member, and
wherein when the electric energy generator device receives the emitted ultrasonic-wave, a pressure in the inner space changes, to deform the second friction-charged member to generate a first electric energy via a triboelectric effect between the first and second friction-charged members and a second electric energy via an electromagnetic induction between the upper substrate and the lower substrate.

11. The system of claim 1, wherein the substrate is a lower substrate having a coil buried therein,
wherein the electric energy generator device further comprises an upper electrode disposed on the second friction-charged member, an insulator disposed on the spacer configured to surround the upper electrode and the second friction-charged member, and an upper substrate, which is magnetic, disposed on the upper electrode and the insulator,
wherein a closed inner space is defined between the first friction-charged member and the second friction-charged member and the spacer,
wherein when the electric energy generator device receives the emitted ultrasonic-wave, a pressure in the inner space changes, to deform the second friction-charged member to generate a first electric energy via a triboelectric effect between the first and second friction-charged members and a second electric energy via an electromagnetic induction between the upper and lower substrates.

12. An electric energy generator system comprising:
an ultrasonic-wave emission device configured to generate an ultrasonic-wave and emit the ultrasonic-wave; and
an electric energy generator device configured to generate an electric energy upon a receipt of the emitted ultrasonic-wave,
wherein the electric energy generator device comprises:
a lower substrate;
a lower electrode on the lower substrate;
a piezoelectric layer on the lower electrode;
an upper electrode on the piezoelectric layer;
an insulator disposed on the lower substrate and configured to surround the lower electrode, the piezoelectric layer and the upper electrode; and
an upper substrate disposed on the upper electrode and the insulator.

13. The system of claim 12, further comprising a load electrically coupled to the lower electrode and the upper electrode.

14. The system of claim 13, further comprising a rectifier diode electrically coupled to and at least one of between the lower electrode and the load and:
between the upper electrode and the load.

15. An electric energy generator system comprising:
an ultrasonic-wave emission device configured to generate an ultrasonic-wave and emit the ultrasonic-wave; and
an electric energy generator device configured to generate an electric energy upon a receipt of the emitted ultrasonic-wave,
wherein the electric energy generator device comprises:
a lower substrate;
a lower electrode disposed on the lower substrate;
at least one electret disposed on the lower electrode;
a spacer disposed on the lower substrate and configured to surround the lower electrode; and
an upper substrate disposed on the spacer.

16. The system of claim 15, wherein the at least one electret comprises a first electret disposed on the lower electrode and a second electret, which has opposite polarization direction from the first electret, disposed on the spacer to be spaced from the first electret,
wherein the system further comprises an upper electrode disposed on the second electret, and an insulator disposed on the spacer and configured to surround the second electret and the upper electrode,
wherein a closed inner space is defined between the first electret and the second electret and the spacer, and
wherein when the electric energy generator device receives the emitted ultrasonic-wave, a pressure in the inner space changes, to change a spacing between the first electret and the second electret to generate an electric energy.

17. The system of claim 15, wherein the at least one electret is surrounded by the spacer,
wherein the system further comprises an upper electrode disposed on the spacer to be separated from the at least one electret, and an insulator disposed on the spacer and configured to surround the upper electrode,
wherein a closed inner space is defined between the at least one electret and the upper electrode and the spacer,
wherein when the electric energy generator device receives the emitted ultrasonic-wave, a pressure in the inner space changes, to change a spacing between the at least one electret and the upper electrode to generate an electric energy.

18. The system of claim 15, wherein the system further comprises an upper electrode disposed on the at least one electret, and an insulator disposed on the spacer and configured to surround the at least one electret and the upper electrode,
wherein a closed inner space is defined between the at least one electret and the lower electrode and the spacer,
wherein when the electric energy generator device receives the emitted ultrasonic-wave, a pressure in the inner space changes, to change a spacing between the at least one electret and the lower electrode to generate an electric energy.

19. The system of claim 15, wherein the at least one electret comprises a first electret disposed on the lower electrode and a second electret, which has opposite polarization direction from the first electret, disposed on the spacer to be spaced from the first electret, wherein the lower substrate has a coil buried therein, and the upper substrate is magnetic, wherein a closed inner space is defined between the first electret and the second electret and the spacer, wherein when the electric energy generator device receives the emitted ultrasonic-wave, a pressure in the inner space changes, to change a spacing between the first electret and the second electret, to generate a first electric energy via a potential difference using the first electret and the second electret, and a second electric energy via an electromagnetic induction between the upper and lower substrates.

20. The system of claim 16, wherein the upper substrate has a coil buried therein, and the upper substrate is magnetic, wherein a closed inner space is defined between the first electret and the second electret and the spacer, wherein when the electric energy generator device receives the emitted ultrasonic-wave, a pressure in the inner space changes, to change a spacing between the first electret and the second electret, to generate a first electric energy via a potential difference using the first electret and the second electret, and a second electric energy via an electromagnetic induction between the upper and lower substrates.

* * * * *